United States Patent [19]
Thompson

[11] Patent Number: 6,010,448
[45] Date of Patent: Jan. 4, 2000

[54] EMBRYO TRANSFER ARRANGEMENT

[75] Inventor: Ronald J. Thompson, Ft. Thomas, Ky.

[73] Assignee: MedWorks Corp, Louisville, Ky.

[21] Appl. No.: 09/110,928

[22] Filed: Jul. 6, 1998

Related U.S. Application Data

[63] Continuation-in-part of application No. 09/023,265, Feb. 13, 1998, which is a continuation-in-part of application No. 08/953,063, Oct. 17, 1997.

[51] Int. Cl.[7] .................................................. A61B 17/43
[52] U.S. Cl. ............................................. 600/34; 600/114
[58] Field of Search ................................ 600/33–35, 114; 604/54, 55

[56] References Cited

U.S. PATENT DOCUMENTS

| | | | |
|---|---|---|---|
| 5,360,389 | 11/1994 | Chenette | 600/34 |
| 5,472,419 | 12/1995 | Bacich | 600/35 X |
| 5,656,010 | 8/1997 | Li et al. | 600/34 |

*Primary Examiner*—Samuel Gilbert
*Attorney, Agent, or Firm*—Don Halgren

[57] ABSTRACT

The present invention comprises a method and apparatus for implantation of an embryo by a flexible delivery catheter onto a pre-selected optimum site on the endometrium of a female uterus. The method comprises the steps of securing the embryo onto the endometrium of the uterus with an adhesive carried by a distal end of the flexible catheter, and depositing the embryo in a medium of Hyaluronic Acid prior to its disposition onto the endometrium of the uterus. The method also includes the steps of positioning the flexible delivery catheter within the uterus, under the guidance of a flexible visualization device carried by the catheter, and arranging a plurality of lumens within the catheter to permit the introduction of the adhesive medium through one lumen, and the visualization device through another of the lumens, to permit the delivery site selection.

16 Claims, 3 Drawing Sheets

EMBRYO TRANSFER ARRANGEMENT

This application is a continuation-in-part application of my earlier co-pending U.S. patent application filed Feb. 1998, Ser. No. 09/023,265 pending, which is a continuation-in-part application of my co-pending U.S. patent application Ser. No. 08/953,063, filed Oct. 17, 1997, pending each of which is incorporated herein by reference, in their entirety.

BACKGROUND OF THE INVENTION

1. Field of the Invention

This invention relates to dispensing instruments and methods for introducing treatment material and fluid-like material with an embryo, into the uterus for the effecting of insemination.

2. Prior Art

The delivery of a treatment medium to an intrauterine locus, particularly for the successful insemination of an egg thereat, is an intended yet elusive goal of many in the medical field. Successful fertilization requires the maturation of spermatozoa in their transit through the uterus and oviducts to the ovum. The goal of the fertilization process is to promote changes in the reproductive tract and increase the ability of sperm to penetrate the egg. This effect is called capacitation.

The likelihood of such fertilization occurs by the successful delivery of the spermatozoa and its association with the extracellular coating of the oval called the zone pellucid. Once a successful motile spermatozoon has fused with the egg membrane, fertilization has been completed. For this to occur however millions of spermatozoa must be successfully released so that one of them reaches the egg at the optimum time. This time window for such spermatozoa within the uterus, from introduction to fertilization, may extend in the range of over a 24 to a 60 hour period.

One approach for delivering material into the female uterus is shown in U.S. Pat. No. 4,182,328 to Bolduc et al. This patent shows a dispensing instrument utilizing a balloon which is inflated within the uterus. A piston and cylinder arrangement has a duct that extends through the balloon which feeds the material to the uterus. The material is delivered over a short period of time and the balloon and probe are readily withdrawn thereafter. A further concept to Bolduc, is shown in U.S. Pat. No. 4,547,188 with a complicated housing and injector assembly with a conduit path through a balloon for treatment of a female uterus.

U.S. Pat. No. 4,654,025 to Cassou et al. discloses an insemination apparatus for animals, utilizing a flexible injector probe, having a plurality of expandable balloons one end of each arranged to facilitate injection of semen from a reservoir tube into the vaginal cavity of the animal. U.S. Pat. No. 5,104,377, to Levine et al., shows a device for accessing and introducing fluids into the female uterus. This device uses several spaced apart balloons to securely couple the shaft to the uterus, adjusting to the length of the cervical canal. U.S. Pat. No. 5,372,584 to Zink et al., shows an apparatus for establishing access to the uterus and fallopian tubes of a female. An anchoring tube on the end of the flexible catheter is first inserted within the uterus. After such anchoring is competed, the elongated second catheter is arranged to extend through the first catheter and balloon and into the fallopian tubes. Injection of treatment into those fallopian tubes is thereby accomplished. U.S. Pat. No. 5,562,654 to Smith et al. shows an arrangement for time released delivery of a preparation into a uterine cavity. An osmotic pump is located within the vagina of the female, having a delivery tube extending within the uterus. An anchoring balloon is disposed about the delivery tube within the uterus and is pressurized through a port which is pressurized through the vagina. Osmotic pressure gradually builds up within the osmotic chamber to pressurize an inner chamber to deliver material from the vagina to within the uterus through the delivery tube.

It is an object of the present invention to overcome the limitations and objections of the prior art.

It is a further object of the present invention, to provide a unique method and apparatus for the treatment of a mammalian uterus, in a safe and comfortable manner for the delivery and development of an embryo there within.

It is still yet a further object of the present invention, to provide a unique method and apparatus for the implantation of a human or animal female where unnecessary medical procedures are eliminated.

BRIEF SUMMARY OF THE INVENTION

The present invention relates to an apparatus and method for utilizing that apparatus for the implantation of an embryo against the endometrium of the female uterus.

In a first preferred embodiment of the present invention, an elongated flexible, three lumen catheter is arranged, having a distal end which is insertable within the female uterus. The catheter has a proximal end which is attachable to an arrangement of pressure/supply syringes. The distal end of the catheter is insertable into the uterus so that an opening of a supply lumen is in juxtaposition with the endometrium thereat. A visualization lumen in the catheter has an optical fiber and a light source arranged therethrough. A syringe at the proximal end of the catheter may be arranged to pressurize and/or inject an embryo through an embryo placement supply lumen also in the catheter. The embryo may also be "preloaded" into the distalmost end of the supply lumen prior to introduction of the catheter into the uterus. In either case, the embryo is implanted into the endometrium within the uterus. Visualization of this process through an eyepiece at the proximal end of the optical fiber will corroborate implantation of the embryo thereat. A second syringe is arranged in communication at the proximal end of the catheter, with the third lumen, for the disposition of a plug of Hyaluronic Acid through that third lumen, and onto the implanted embryo previously discharged onto the endometrium within the uterus. Visualization through the optical fiber again permits the accurate and controlled discharge of the Hyaluronic Acid plug onto the embryo so as to securely attach that embryo in place, and to provide a medium for a gel-like tissue adhesive at the optimum anatomical site within the uterus. This placement of the embryo and the gluing of that embryo to the endometrium by a tissue adhesive gel, which activates by exposure to the moist environment of the endometrium increases the chance of survival and growth of that embryo.

A second preferred embodiment of the present invention comprises an elongated flexible balloon catheter having a proximal and a distal end. The distal end of the flexible balloon catheter of the present invention includes a generally triangularly shaped balloon wrapped therearound, and held in place against the catheter shaft by a flexible polymeric sheath which permits the wrapped balloon to be comfortably inserted within the walls of the uterus. The distalmost end of the wrapped balloon contains a generally hemispherically shaped cavity, having a gel-like Hyaluronic Acid substance with an embryo disposed therewithin. Retraction of the sheath from the balloon by sliding it proximally also removes the distalmost end of the sheat from the distalmost end of that catheter, permitting presentation of the embryo onto the endometrium in the uterine wall.

An inflation lumen is connected to the proximalmost end of the balloon, so as to permit the balloon to be inflated within the uterus, and permitting the plug of Hyaluronic Acid and the embryo to be pressed against the endometrium. An optical fiber may be arranged between the sheath and the wrapped balloon, so as to permit the visualization of the implantation of the encapsulated embryo against the endometrium as the sheath is removed therefrom. After the embryo has been adhered to the endometrium, the balloon is deflated through its inflation/deflation lumen of the catheter shaft, and the balloon is withdrawn from the uterine cavity, leaving the embryo and Hyaluronic Acid adhesive substance in place therewithin for the intended embryo growth and maturation.

A further preferred embodiment of the present invention is similar to that of the aforementioned embodiment. However, the apparatus herein includes the balloon being of a biodegradable substance, made from a material such as a film of Hyaluronic Acid. Upon proximal withdrawal of a sheath from around the outer edge of the distal end of the elongated flexible catheter carrying the Hyaluronic Acid biodegradable balloon within the uterus, and subsequent to visualization of the proper placement of the embryo against the endometrium, the flexible catheter shaft is gently withdrawn from within the expanded inflated balloon leaving therein, a closed valve, (a duckbill valve). Upon removal of the catheter shaft and the stem portion leading into the valve of the balloon, the biodegradable balloon is left in place dissolving after a period of between 12 and 24 hours, leaving the embryo properly implanted against the uterine wall. Thus there has been shown an arrangement for the implantation of an embryo against the uterine wall, by an apparatus which permits the visualization and safe implantation at an optimal site therewithin. By the use of a gel-like adhesive medium, such as Hyaluronic Acid, such implantation is fostered and growth and survival is improved over those procedures and apparatus shown in the prior art.

Thus the invention includes a method of implantation of an embryo by a flexible delivery catheter onto a pre-selected optimum site on the endometrium of a female uterus, comprising the steps of: securing the embryo onto the endometrium of the uterus with an adhesive carried by a distal end of the flexible catheter, depositing the embryo in a medium of Hyaluronic Acid prior to its disposition onto the endometrium of the uterus, positioning said flexible delivery catheter within the uterus, under the guidance of a flexible visualization device carried by said catheter, arranging a plurality of lumens within the catheter to permit the introduction of the adhesive medium through one lumen, and the visualization device through another of the lumens, to permit the delivery site selection, wrapping an inflatable balloon about the distal end of the catheter, and arranging one of the lumens to be in communication therewith, so as to permit inflation of the balloon in the uterus after the balloon has been guided to a pre-selected situs therein, placing a flexible sheath about the balloon wrapped about the distal end of the catheter, to permit the balloon to be safely introduced into the uterus prior to its inflation therein, aligning the visualization device between the sheath and the wrapped balloon to permit site selection of the endometrium in the uterus as the catheter is being introduced into the uterus by the operator of the catheter, and arranging a cavity in the distal end of the catheter for the carrying of an embryo and adhesive medium therein, for delivery to the endometrium of the uterus. The method also includes placing an embryo and an adhesive medium into the cavity in the distal end of the catheter and sliding the sheath proximally so as to expose the embryo and adhesive to the preselected endometrium situs of the uterus. The method also includes securing the embryo onto the endometrium of the uterus with an adhesive carried by a distal end of said flexible catheter, depositing the embryo in a medium of Hyaluronic Acid prior to its disposition onto the endometrium of the uterus, positioning the flexible delivery catheter within the uterus under the guidance of a flexible visualization device carried by the catheter. The method also includes the steps of arranging a plurality of lumens within the catheter to permit the introduction of the adhesive medium through one lumen, and the visualization device through another of the lumens, to permit delivery site selection.

BRIEF DESCRIPTION OF THE DRAWINGS

The objects and advantages of the present invention will become more apparent, when viewed in conjunction with the following drawings, in which.

DESCRIPTION OF THE PREFERRED EMBODIMENTS

Figures 1, 2:
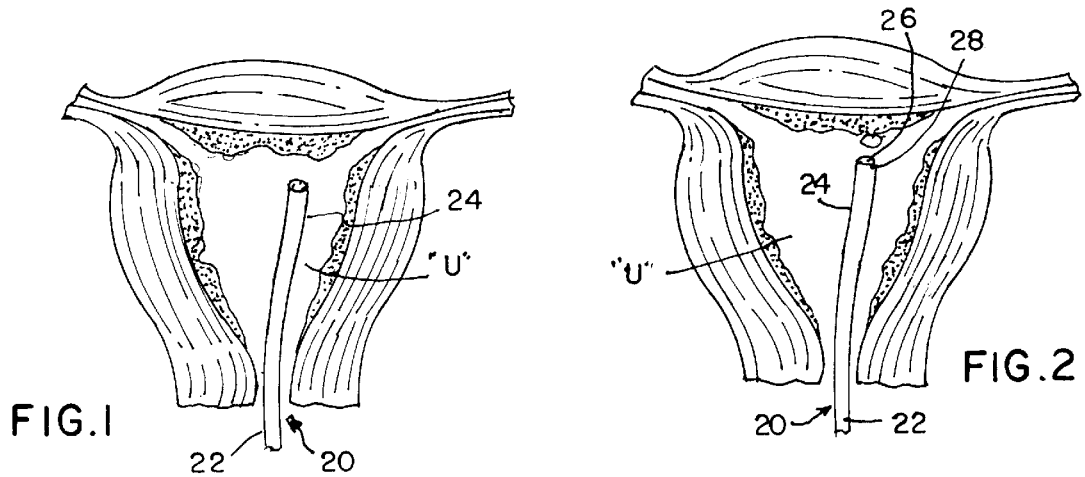
FIG. 1 is a side representational view of a uterus, showing a flexible three lumen catheter constructed according to the principles of the present invention, introduced therein.
FIG. 2 is a view similar to that shown in FIG. 1, showing the delivery and implantation of an embryo against the uterine wall.

Referring now to the drawings in detail, and particularly to FIG. 1, there is shown the present invention which comprises a catheter apparatus 20 and method for utilizing that catheter apparatus 20 for the implantation of an embryo "E" against the endometrium wall of the female uterus "U".

Figures 3, 4:
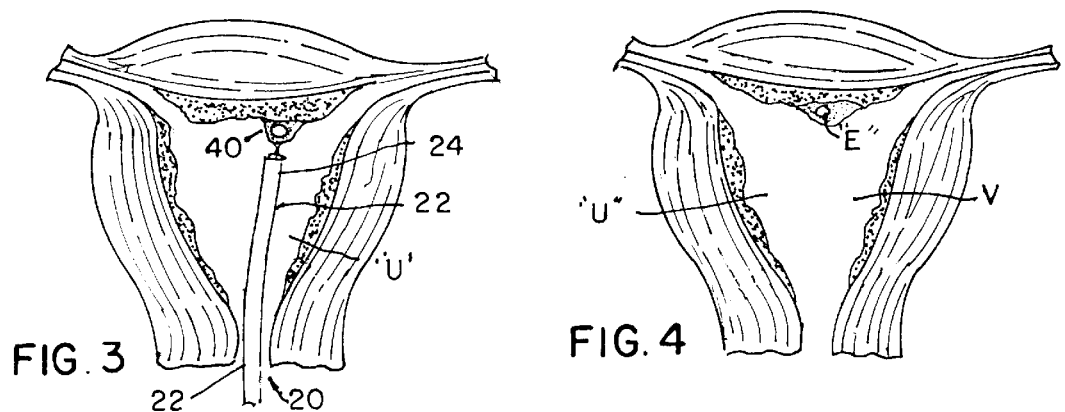
FIG. 3 is a view similar to FIG. 2, showing the introduction of a gel-like material to secure an embryo in place, against the uterine wall.
FIG. 4 is a view similar to that shown in FIG. 3, showing an embryo in place, held therein by a gel-like substance.
Figure 3A:
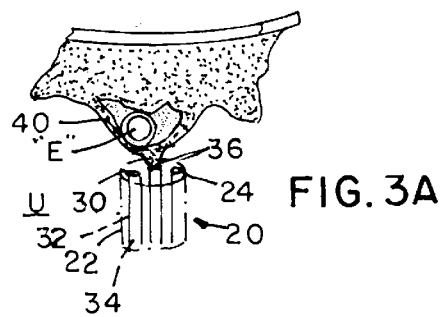
FIG. 3A is an enlarged elevational view of a portion of the uterus and catheter delivery apparatus shown in FIG. 3.

In a first preferred embodiment of the present invention, the catheter apparatus 20 includes an elongated, flexible, three lumen catheter 22 is arranged to have a distal end 24 which is insertable within the female uterus "U", as shown in FIG. 1, through the vagina. The catheter 22 has a proximal end, not shown for clarity, which is attachable to an arrangement of pressure/supply syringes. The distal end 24 of the catheter 22 is insertable into the uterus "U" so that an opening 26 of a supply lumen 28 in the catheter 22 is in juxtaposition with the endometrium, as shown in FIG. 2. A visualization lumen 30 in the catheter 22 has an optical fiber 32 and a light source 34 arranged therethrough. A syringe (not shown for clarity) at the proximal end of the catheter 20 may be arranged to pressurize and/or inject an embryo "E" through an embryo placement supply lumen 28 also in the catheter 22. The embryo "E" may also be "preloaded" into the distalmost end of the supply lumen 28 prior to introduction of the catheter apparatus 20 into the uterus "U". In either case, the embryo "E" is implanted into the endometrium within the uterus "U". Visualization of this process through an eyepiece at the proximal end of the optical fiber 34 will corroborate implantation of the embryo "E" thereat. A second syringe (not shown for clarity) is arranged in communication at the proximal end of the catheter apparatus 20, with the third lumen 36, for the introduction and disposition of a plug of Hyaluronic Acid 40 through that third lumen 36, and onto the implanted embryo "E", previously discharged onto the endometrium within the uterus "U", as represented in FIGS. 3 and 3A. Visualization through the optical fiber 34 again permits the accurate and controlled discharge of the plug of Hyaluronic Acid 40 onto the embryo "E" so as to securely attach that embryo "E" in place, and to provide a medium for a gel-like tissue adhesive at the optimum anatomical site within the uterus "U" as represented by FIG. 4. This placement of the embryo "E" and the gluing of that embryo "E" to the endometrium by a tissue adhesive gel 40, which activates by exposure to the moist environment of the endometrium, increases the chance of survival and growth of that embryo "E".

Figure 5:
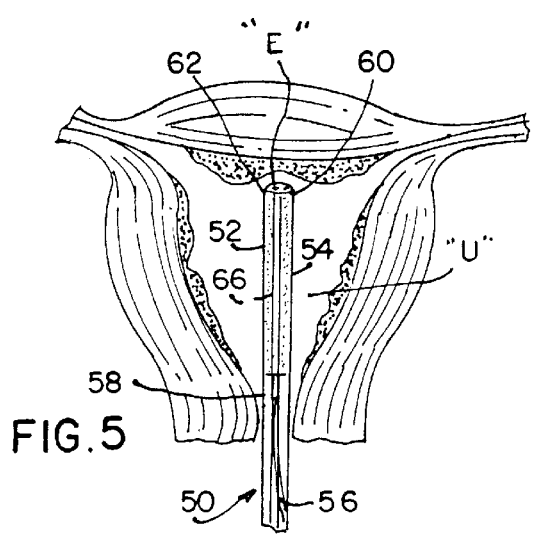
FIG. 5 is a side elevational representational view of a uterus, showing the introduction of a balloon delivery catheter therewithin.
Figure 6:
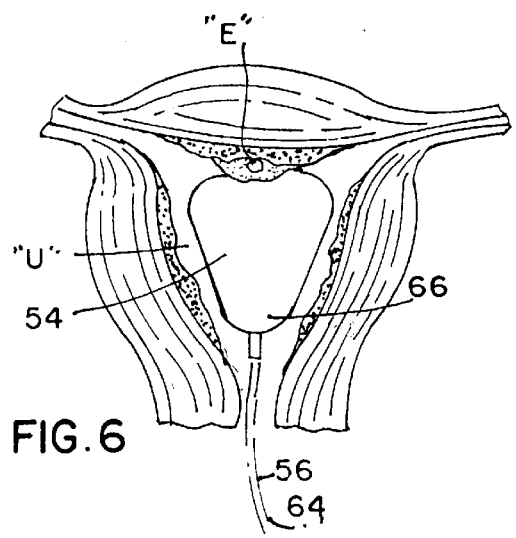
FIG. 6 is a view similar to that of FIG. 5, showing a balloon of the balloon delivery catheter inflated within the uterus.
Figure 7:
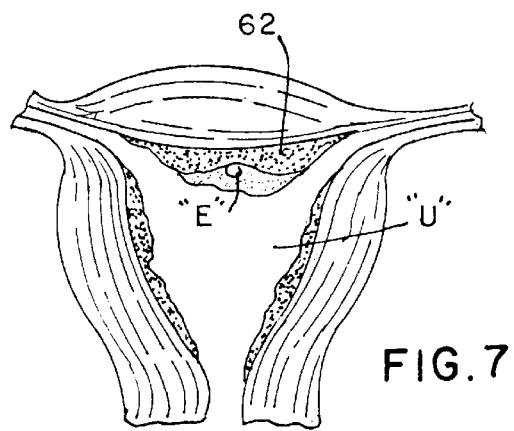
FIG. 7 is a view similar to that of FIG. 6, showing an embryo and its gel-like adhesive substance holding that embryo in place against the uterine wall.

A second preferred embodiment of the present invention 20, as represented by FIGS. 5, 6 and 7, comprises an elongated flexible balloon catheter 50 having a proximal end (not shown for clarity), and a distal end 52. The distal end 52 of the flexible balloon catheter 50 of the present invention includes a generally truncated balloon 54 wrapped therearound, and held in place against the catheter shaft 56 by a flexible polymeric sheath which permits the wrapped balloon 54 to be comfortably inserted within the walls of the uterus "U". The distalmost end of the wrapped balloon 54 is formed into a generally hemispherically shaped holding cavity 60, having a gel-like Hyaluronic Acid medium 62 with an embryo "E" disposed therewithin. Retraction of the sheath 58 from the balloon 54 is accomplished by sliding it proximally to also remove the distalmost end of the sheath 58 from the distalmost end 52 of that catheter 56, permitting presentation of the embryo "E" onto the endometrium in the uterine wall, as represented in FIGS. 5 and 6.

An inflation lumen 64 in the catheter 56 is connected to the proximalmost end 66 of the balloon 54, so as to permit the balloon 54 to be inflated as it is positioned within the uterus "U", and permitting the plug of Hyaluronic Acid 62 and the embryo "E" to be pressed against the endometrium. An elongated optical fiber 66 (having an eyepiece at its proximal end, not shown for clarity), may be aligned between the sheath 58 and the wrapped balloon 54, and into a lumen in the catheter so as to permit the visualization of the implantation of the encapsulated embryo "E" against the endometrium as the sheath is removed therefrom. After the embryo has been adhered to the endometrium, as represented in FIG. 6, the balloon 54 is deflated through its inflation/deflation lumen of the catheter shaft 56, and the balloon 54 is withdrawn from the uterine cavity, leaving the embryo and Hyaluronic Acid medium 62 adhesively in place therewithin for the intended embryo growth and maturation.

Figure 8:
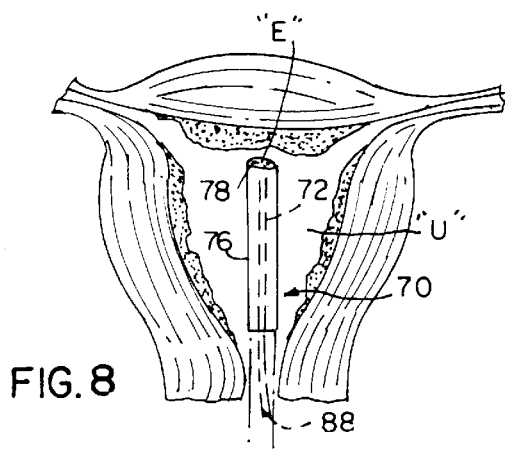
FIG. 8 is a view similar to that of FIG. 5, showing a biodegradable balloon introduced into the uterus for the delivery of an embryo there within.
Figure 9:
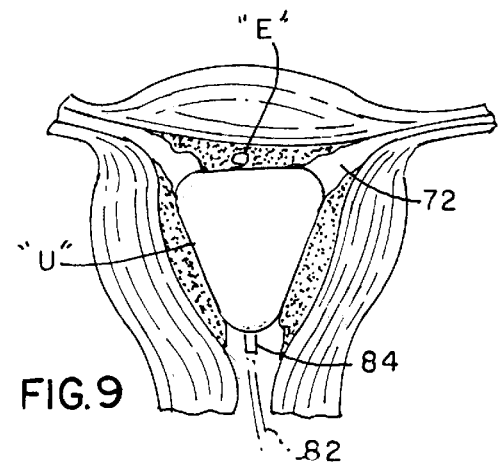
FIG. 9 is a view similar to that of FIG. 6, showing the embryo delivered into the uterus and an inflated balloon expanded thereadjacent, the inflated balloon holding the embryo against the uterine wall.
Figure 10:
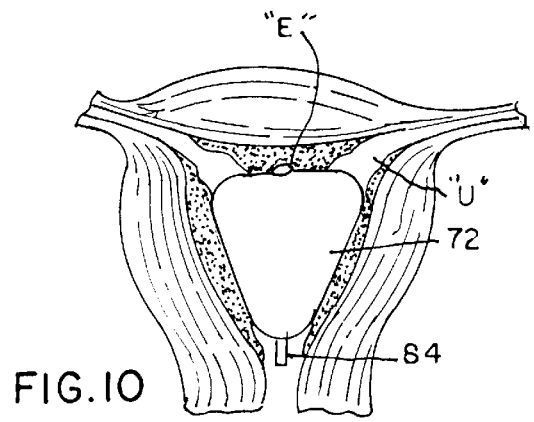
FIG. 10 is a view similar to that of FIG. 9, showing the inflated balloon within the uterine cavity with the delivery catheter and inflationary stem removed therefrom.
Figure 11:
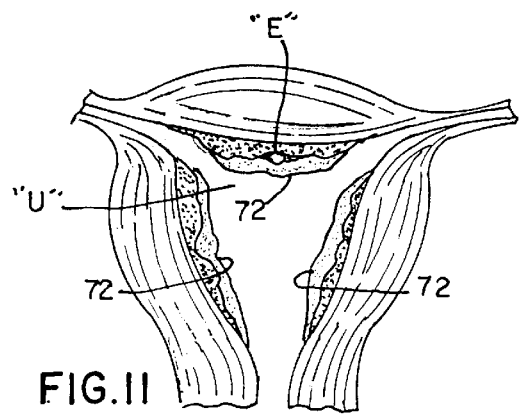
FIG. 11 is a view similar to that of FIG. 10, showing the embryo implanted in the uterine wall with its gel-like adhesive glue holding the embryo thereto, and the delivery balloon being dissolved leaving only the Hyaluronic Acid residue therebehind.

A further preferred embodiment of the present catheter apparatus 70 is shown in FIGS. 8, 9, 10 and 11, which catheter apparatus 70 is similar to that of the aforementioned embodiment. However, the apparatus herein includes the balloon 72 now formed from a sheet of a biodegradable substance, that is, a material such as a film of Hyaluronic Acid 74. A hemispherically shaped cavity 73 is arranged at the distalmost end of the of Hyaluronic Acid balloon 72, and is pre-loaded with an embryo "E" for implantation into the endometrium of the uterus "U" as represented in FIG. 8. Upon proximally directed withdrawal of a sheath 76 from around the outer edge of the distal end 78 of the elongated flexible catheter 70 carrying the Hyaluronic Acid biodegradable balloon 72, the embryo surrounded by the plug of Hyaluronic Acid 71 within the cavity 73 is exposed to and deposited onto an optimum location of the endometrium of the uterus. The placement of the embryo "E" within the uterus "U", is accomplished by visualization of the endometrium (through the proximal eyepiece an optical fiber 80 aligned between the balloon 72 and the sheath 76). After such placement of the embryo "E", the flexible catheter shaft 82 is gently withdrawn from within the expanded inflated balloon 72 leaving therein, a closed (dissolvable) duckbill type valve 84. Upon removal of the catheter shaft 82 and the stem portion leading into the valve 84 of the Hyaluronic Acid balloon 72, as represented in FIG. 10, that biodegradable balloon 72 is left in place, to dissolve after a period of between 12 and 24 hours, to sustain and leave the embryo properly implanted against the uterine wall for its most tenuous period, that is, the initial implantation period, as represented in FIG. 11.

Thus there has been shown an arrangement for the implantation of an embryo against the uterine wall, by an apparatus which permits the visualization and safe implantation at an optimal site therewithin. By the use of a gel-like adhesive medium, such as Hyaluronic Acid, by an inflation balloon and/or a site specific adhesive/growth medium, such implantation is fostered and growth and survival is improved over those procedures and apparatus shown in the prior art.

I claim:

1. A method of implantation of an embryo by a flexible delivery catheter onto a pre-selected optimum site on the endometrium of a female uterus, comprising the step of:

providing a flexible delivery catheter for use in said female uterus;

securing the embryo onto the endometrium of the uterus with an adhesive carried by a distal end of said flexible catheter.

2. The method of implantation of an embryo, as recited in claim 1, including the step of:

depositing the embryo in a medium of Hyaluronic Acid prior to its disposition onto the endometrium of the uterus.

3. The method of implantation of an embryo, as recited in claim 2, including the step of:

positioning said flexible delivery catheter within the uterus, under the guidance of a flexible visualization device carried by said catheter.

4. The method of implantation of an embryo, as recited in claim 3, including the step of:

arranging a plurality of lumens within said catheter to permit the introduction of said adhesive medium through one lumen, and said visualization device through another of said lumens, to permit said delivery site selection.

5. The method of implantation of an embryo as recited in claim 4, including the step of:

wrapping an inflatable balloon about said distal end of said catheter, and arranging one of said lumens to be in communication therewith, so as to permit inflation of said balloon in the uterus after said balloon has been guided onto said pre-selected optimum site therein.

6. The method of implantation of an embryo as recited in claim 5, including the step of:

placing a flexible sheath about said balloon wrapped about said distal end of said catheter, to permit said balloon to be safely introduced into the uterus prior to its inflation therein.

7. The method of implantation of an embryo as recited in claim 6, including the step of:

aligning said visualization device between said sheath and said wrapped balloon to permit site selection of the endometrium in said uterus as said catheter is being introduced into the uterus by the operator of said catheter.

8. The method of implantation of an embryo as recited in claim 6, including the step of:

arranging a cavity in said distal end of said catheter for the carrying of an embryo and adhesive medium therein, for delivery to the endometrium of the uterus.

9. The method of implantation of an embryo as recited in claim 8, including the step of:

placing an embryo and an adhesive medium into said cavity in said distal end of said catheter.

10. The method of implantation of an embryo as recited in claim 8, including the step of:

sliding said sheath proximally so as to expose said embryo and adhesive to the preselected endometrium situs of the uterus.

11. The method of implantation of an embryo as recited in claim 5, including the step of:

forming said balloon from a layer of film comprised of a glycosaminoglycan.

12. A method of implantation of an embryo by a flexible delivery catheter onto a preselected optimum site on the endometrium of a female uterus, comprising the step of:

providing a flexible visualization device with a proximal end and a distal end;

selecting said pre-selected site for said embryo implantation on the endometrium of the uterus by insertion of said distal end of said flexible visualization device in said uterus;

viewing said uterus through said flexible insertion device and securing the embryo onto the pre-selected site on the endometrium of the uterus with an adhesive carried by a distal end of said flexible delivery catheter.

13. The method of implantation of an embryo, as recited in claim 12, including the step of:

providing a flexible catheter;

depositing the embryo in a medium of Hyaluronic Acid prior to its disposition onto the endometrium of the uterus.

14. The method of implantation of an embryo, as recited in claim 13, including the step of:

positioning said flexible delivery catheter within the uterus, under the guidance of said flexible visualization device carried by said catheter.

15. The method of implantation of an embryo, as recited in claim 13, including the step of:

delivering said embryo to said uterus through said deliver catheter.

16. The method of implantation of an embryo, as recited in claim 15, including the step of:

arranging a plurality of lumens within said catheter to permit the introduction of said adhesive medium through one lumen, and said visualization device through another of said lumens, to permit said delivery site selection.

* * * * *